United States Patent
Honkanen

(10) Patent No.: US 11,788,936 B2
(45) Date of Patent: Oct. 17, 2023

(54) METHOD FOR TREATING A LIQUID SAMPLE IN ORDER TO REMOVE INTERFERENCE BY IRON

(71) Applicant: Kemira Oyj, Helsinki (FI)

(72) Inventor: Tapio Honkanen, Porvoo (FI)

(73) Assignee: Kemira Oyj, Helskinski (FI)

(*) Notice: Subject to any disclaimer, the term of this patent is extended or adjusted under 35 U.S.C. 154(b) by 1426 days.

(21) Appl. No.: 15/999,850

(22) PCT Filed: Feb. 17, 2017

(86) PCT No.: PCT/FI2017/050104
§ 371 (c)(1),
(2) Date: Aug. 20, 2018

(87) PCT Pub. No.: WO2017/140995
PCT Pub. Date: Aug. 24, 2017

(65) Prior Publication Data
US 2021/0215578 A1 Jul. 15, 2021

(30) Foreign Application Priority Data
Feb. 19, 2016 (FI) .................................... 20165133

(51) Int. Cl.
C09K 8/528 (2006.01)
G01N 1/22 (2006.01)
E21B 37/06 (2006.01)
G01N 1/34 (2006.01)
G01N 1/38 (2006.01)

(52) U.S. Cl.
CPC .......... *G01N 1/2202* (2013.01); *C09K 8/528* (2013.01); *E21B 37/06* (2013.01); *G01N 1/34* (2013.01); *G01N 1/38* (2013.01); *C09K 2208/28* (2013.01); *C09K 2208/32* (2013.01); *G01N 2001/222* (2013.01)

(58) Field of Classification Search
CPC .......... G01N 1/2202; G01N 1/34; G01N 1/38; G01N 2001/222; G01N 33/84; C09K 8/528; C09K 2208/28; C09K 2208/32; E21B 37/06
See application file for complete search history.

(56) References Cited

U.S. PATENT DOCUMENTS 6,420,530 B1   7/2002 Weatherby et al.

FOREIGN PATENT DOCUMENTS

| ES | 2258393 | * | 6/2007 | |
| ES | 2258393 B1 | * | 6/2007 | ............... C02F 1/58 |
| WO | 2015075309 | | 5/2015 | |

OTHER PUBLICATIONS

Sandra, et al, Demetalation of Fe, Mn, and Cu chelates and complexes: Application to the NMR analysis of micronutrient fertilizers, J. Agric. Food Chem, 2011, 59, 13110-13116.*
XP-002769657, dated 1969.*
ISSN 0216-3128 , dated 2007.*
Peynaud E, "3 years of the use of ascorbic acid in wine treatment. (translated)", FSTA Database accession No. FS-1970-01-H-0157 Vini D'Italia,vol. 11, No. 61, 1969, p. 283, abstract. 1 sheet.
Lopez-Rayo S et al, "Demetalation of Fe, Mn, and Cu chelates and complexes: Application to the NMR analysis of micronutrient fertilizers", Journal of Agricultural and Food Chemistry Dec. 28, 2011 American Chemical Society USA,vol. 59, No. 24, Dec. 28, 2011 (Dec. 28, 2011), p. 13110-13116.
Neil Poynton et al, "Development of a New Tagged Polymeric Scale Inhibitor with Accurate Low-level Residual Inhibitor Detection, for Squeeze Applications", SPE International Conference on Oilfield Scale,May 30, 2012 (May 30, 2012).

* cited by examiner

*Primary Examiner* — Kumar R Bhushan
(74) *Attorney, Agent, or Firm* — Robin L. Teskin; Baker, Donelson, Bearman, Caldwell & Berkowitz PC

(57) ABSTRACT

The invention relates to a method for treating a liquid sample, which comprises disturbing iron and at least one organic compound of interest. The, the method comprises addition of a reagent comprising an ammonium salt, alkali metal salt or earth alkali metal salt of hexacyanoferrate to the sample. Iron in the sample is allowed to interact with the reagent and to form a reaction product, the reaction product of iron is separated from the sample, and the amount of the at least one compound of interest is determined from the sample. The invention relates also to use of salt of hexacyanoferrate.

19 Claims, No Drawings

METHOD FOR TREATING A LIQUID SAMPLE IN ORDER TO REMOVE INTERFERENCE BY IRON

PRIORITY

This application is a U.S. national application of the international application number PCT/FI2017/050104 filed on Feb. 17, 2016 and claiming priority of Finnish national application FI 20165133 filed on Feb. 19, 2016, the contents of all of which are incorporated herein by reference.

The present invention relates to a method for treating an acidic liquid sample and use of hexacyanoferrate according to the preambles of the enclosed independent claims.

Organic compounds, such as synthetic organic compounds, are used in many industrial processes as process chemicals and/or process aids. For example, scale inhibitors are used in oil production for stimulation of the oil wells, for controlling and/or preventing scale depositions. Similar compounds are also used in many mining processes. The concentration of the organic compound in the process should be sufficiently high in order to provide the desired effect or reaction. On the other hand, the use of excess amounts of chemicals is uneconomical and non-sustainable. Consequently, it is important to obtain reliable knowledge about the concentration of the organic compound in the process for securing proper function of the process.

A number of different test methods and test kits are developed for determining the concentration of various organic compounds in process circulation. For example, international patent applications WO 2015/075308 and WO 2015/075309 disclose methods where scale inhibitors are allowed to interact with a reagent comprising a lanthanide (III) ion and the concentration of the scale inhibitor is determined by using an excitation signal from the sample. However, many process environments comprise ions and/or compounds that disturb the determination of the desired organic compound. For example, iron is present, sometimes abundantly, in many oil and mining processes, in form of iron(II) and/or in form of iron(III). In these processes, there is a need to pre-treat liquid samples from the process before determination of the organic compound. Consequently, there is a constant need for new treatment methods for liquid samples, with which methods the interferences from disturbing ions and compounds can be minimised in succeeding quantitative determination of organic compounds. Proper determination of the organic compounds used in the process improves the process economy as excessive use is avoided as well as prevents process disturbances due to too small dosage.

It is an object of the present invention to reduce or even eliminate the problems appearing in prior art.

An object of the present invention is to provide a simple and effective method for treating an industrial process sample in order to minimise possible iron interference.

In a typical method according to the present invention for treating a liquid sample comprising disturbing iron and at least one organic compound of interest, the method comprises adding a reagent comprising an ammonium salt, alkali metal salt or earth alkali metal salt of hexacyanoferrate to the sample, allowing iron in the sample to interact with the reagent and to form a reaction product, separating the reaction product of iron from the sample, and determining the amount of the at least one compound of interest from the sample.

Typical use according to the present invention of an alkali metal salt, ammonium salt or earth alkali metal salt of hexacyanoferrate, preferably potassium hexacyanoferrate, is for pre-treating a liquid sample, which comprises disturbing iron and at least one organic compound of interest.

Now it has been surprisingly found that a reagent comprising a suitable salt of hexacyanoferrate interacts with iron in a liquid sample and produces a reaction product which can be easily separated from the sample. In this manner the interference from iron is minimised, sometimes completely eliminated, and the organic compound of interest in the liquid sample can be analysed, for example by using methods described in WO 2015/075308 and WO 2015/075309. It was unexpected that the disturbing iron can be so effectively and simply removed, without any complicated process steps, even when the sample matrix is relatively complex, as is often case with process samples, especially from oil and mining industry.

The present invention is suitable for samples, which comprise iron in form of iron(II) or iron(III) or both in form of iron(II) and iron(III). The total concentration of iron may be >0.5 ppm, preferably >10 ppm, more preferably >20 ppm, even more preferably >30 ppm, yet more preferably >50 ppm, even possibly >75 ppm, sometimes even >100 ppm, calculated as a sum of iron(II) and iron(III). The invention is suitable for all liquid samples comprising iron, irrespective if they have either low or high concentration of iron ions, which would otherwise produce a significant interference in the succeeding determination of organic compounds. The method according to the invention is especially suitable for liquid samples having relatively high or high concentration of iron ions, e.g. >20 ppm, and improves significantly the results obtained in succeeding quantitative determination of organic compounds.

According to one embodiment of the invention pH of the sample is adjusted to a pH value≤7, preferably ≤5, more preferably ≤4, even more preferably ≤3, before the addition of the reagent. The pH of the sample may in the range of 1-7, preferably 1-5, more preferably 1-3, even more preferably 1.5-2.5. The acidity of the sample guarantees that the iron remains in ion form and is ready to interact with the reagent when the reagent is added. The pH can be adjusted by addition of suitable strong acid, such as hydrochloric acid.

The reagent may comprise either an ammonium salt, alkali metal salt or earth alkali metal salt of hexacyanoferrate(II) or hexacyanoferrate(III). Suitable alkali metal salts are potassium and sodium salts. Preferably the reagent comprises ammonium hexacyanoferrate or potassium hexacyanoferrate, even more preferably potassium hexacyanoferrate(II).

The reagent is preferably added in such amount that all the iron in the sample interacts with hexacyanoferrate. Preferably the reagent is added in such amount that the hexacyanoferrate is present in slight molar excess to iron in the sample. Preferably the molar ratio of hexacyanoferrate to iron is from 1:2 to 20:1, preferably from 4:5 to 15:1, more preferably 1:1 to 10:1.

The amount of iron in the liquid sample can be determined before addition of the reagent. Any suitable method for quantitatively determining iron can be used. The iron determination may be performed constantly or at predetermined time intervals.

When the amount of iron in the process liquid as a function of time is relatively constant and the amount of iron is not too excessive, it is possible to add a constant amount of reagent to all the samples at various points of sampling time. Typically the amount of iron in the sample is less than 100 ppm when a constant reagent addition is employed. Use of constant reagent amount provides advantages, for example, the method becomes easy to perform and/or automate. Furthermore, it was surprisingly observed that the unreacted reagent comprising unreacted hexacyanoferrate does not interfere with the succeeding determination of the amount of the at least one organic compound of interest.

Alternatively, it is possible to determine for each sample the amount of iron in the sample and to adjust the amount of reagent on basis of the determination result. This alternative is especially suitable if it is known that the amount of iron varies greatly as a function of time, or if the amount of iron in the sample is excessive, for example, >100 ppm, even >150 ppm or >200 ppm. The determination of the amount of iron can be performed regularly at predetermined time intervals.

According to one embodiment of the invention, when iron is in form of iron(II) and the reagent is alkali metal salt of hexacyanoferrate, it is assumed that the following reactions take place (alkali metal indicated as X) with hexacyanoferrate(II):

$$Fe^{2+}+2X^{+}+[Fe(CN)_6]^{4-} \rightarrow X_2Fe[Fe(CN)_6] \quad (1)$$

$$4X_2Fe[Fe(CN)_6]+O_2+4H^{+} \rightarrow 4XFe[Fe(CN)_6]\downarrow +4X^{+}+2H_2O \quad (2)$$

with hexacyanoferrate(III):

$$Fe^{2+}+X^{+}+[Fe(CN)_6]^{3-} \rightarrow XFe[Fe(CN)_6]\downarrow \quad (3)$$

When the alkali metal is potassium the reaction (3) results in Turnbull's blue.

According to one embodiment of the invention, when iron is in form of iron(III) and the reagent is alkali metal salt of hexacyanoferrate, it is assumed that the following reactions take place (alkali metal indicated as X) with hexacyanoferrate(II):

$$Fe^{3+}+X^{+}+[Fe(CN)_6]^{3-} \rightarrow XFe[Fe(CN)_6]\downarrow \quad (4)$$

with potassium hexacyanoferrate(III):

$$Fe^{3+}+[Fe(CN)_6]^{3-} \rightarrow Fe[Fe(CN)_6]\downarrow \quad (5)$$

When the alkali metal is potassium the reaction (4) results in Prussian blue.

According to one preferable embodiment of the invention iron(III) is reduced to iron(II) before the addition of the reagent. The reduction is achieved by addition of a reduction agent to the sample before addition of the reagent and reducing iron(III) to iron(II). Any known reduction agent, which does not interfere with other components of the sample or with the succeeding quantitative determination of the compound of interest, can be used. Suitable reduction agent may be, for example, ascorbic acid or hydroxyl ammonium chloride. The reduction agent may be added in amount, which is 0.1-250 times the amount of iron in moles in the liquid sample, calculated as active reduction agent. It was unexpectedly observed that the reduction agent, such as ascorbic acid, does not interfere with the succeeding determination of the amount of the at least one compound of interest.

Preferably iron, especially iron(II) is allowed to react with the reagent comprising potassium hexacyanoferrate(II). This reaction produces an insoluble precipitated reaction product, which is easy to separate from the liquid sample. The precipitated reaction product may be allowed to sediment, or the reaction product is separated by filtering or by centrifuging, preferably by filtering. Any suitable filtering method may be used. According to one embodiment the precipitated reaction product is filtered by using 0.2 μm or 0.45 μm filter.

According to another embodiment of the invention a flocculation agent is added to the sample after addition of the reagent and separating the reaction product by flocculation. Flocculation is especially used if the reaction product is in form of or comprises colloidal precipitate, such as Turnbull's blue or Prussian blue. Flocculation agent may be anionic or non-ionic polymeric flocculant.

The organic compound of interest may be a synthetic organic compound, a natural polymer or a biopolymer. According to one preferable embodiment the organic compound of interest is an organic compound selected from scale inhibitors, corrosion inhibitors, friction reducers and polymers used in oil field applications and oil recovery processes. Preferably the organic compound of interest is a synthetic organic compound selected from scale inhibitors, corrosion inhibitors, friction reducers and polymers used in oil field applications and oil recovery processes.

According to one preferable embodiment the synthetic organic compound is a scale inhibitor, which comprises at least one ionised group. Scale inhibitors, when added to an aqueous system that tends to form scale, reduce, control, disperse or inhibit the formation, deposition and/or adherence of scale deposits on substrate surfaces in contact with a scale-forming aqueous system.

Preferably scale inhibitor comprises at least one, preferably two or more ionised groups, more preferably at least three ionised groups, even more preferably at least four ionised groups, attached to the scale inhibitor compound structure or polymer/copolymer backbone. According to another exemplary embodiment scale inhibitor comprises one or two ionised groups, per at least some of the monomer units of the scale inhibitor polymer/copolymer. It is not necessary that all monomer units comprise ionised groups. The ionised groups may be selected from phosphates, phosphonates, carboxylates, sulphonates and/or amines, preferably from carboxylates, sulphonates and/or amines. Amines may be primary amines, secondary amines, tertiary amines and/or quaternary amines. Phosphates may be primary phosphates or secondary phosphates. In case the scale inhibitor comprises two or more ionised groups, the ionised groups in the scale inhibitor may all be similar to each other or they may be different from each other. The scale inhibitor may be anionic, cationic or zwitterionic, preferably anionic.

In exemplary embodiments one or more of the ionised groups of the scale inhibitor are capable of interacting with the reagents comprising lanthanide(III) ions. In this context the term "interact" means that the ionised groups can react, coordinate and/or chelate with the reagents comprising lanthanide(III) ions. Especially, the ionised groups of the scale inhibitor can react, coordinate and/or chelate with the lanthanide(III) ions.

According to various embodiments of the invention the scale inhibitor is selected from group comprising polyelectrolyte compounds comprising carboxylate and/or phosphonate groups; homopolymers and copolymers of ethylenically unsaturated acid monomers; organophosphonates; and combinations thereof. The polyelectrolyte compounds may comprise a multiplicity of interactive groups, which can be ionised, for example, carboxylate and/or phosphonate groups. The scale inhibitor may be, for example, a polycarboxylic acid, such as polyacrylic acid, polymethacrylic acid, polymaleic acid or any of their salts with monovalent cations. Alternatively the scale inhibitor may be, for example, maleic anhydride. The scale inhibitor may be a homopolymer or a copolymer of an alpha, beta-ethylenically unsaturated acid monomer such as acrylic acid or methacrylic acid, a diacid such as maleic acid or maleic anhydride, itaconic acid, fumaric acid, monoesters of diacids with alkanols having 1-8 carbon atoms, and/or mixtures thereof. In case the scale inhibitor is a copolymer, it may be composed of two or more co-monomers, and the first co-monomer may be any alpha, beta-ethylenically unsaturated monomer and the second co-monomer may be a non-polar group or monomer, such as styrene or olefinic monomer; or a polar functional group or monomer, such as vinyl acetate, vinyl chloride, vinyl alcohol, an alkyl acrylate, vinyl pyridine, vinyl pyrrolidone, acrylamide or an acrylamide derivative, etc.; or an ionic functional group or monomer, such as styrenesulphonic acid, 2-acrylamido methylpropanesulphonic acid (AMPS), vinylsulphonic acid or vinylphosphonic acid; or a salt of allylsulphonate, such as sodium allyl sulphonate. The scale inhibitor may be an organophosphonate, such as amino tris(methylene phosphonic acid), 1-hydroxy ethylidene-1,1-diphosphonic acid, diethylenetriamine penta(methylene phosphonic acid) or phosphonobutane-tricarboxylic acid.

The scale inhibitor may have any necessary or desired molecular weight. For example, in an exemplary embodiment, the scale inhibitor may have a molecular weight of from about 500 to about 100 000 Daltons, preferably 500 to 100 000 Daltons, more preferably 500-30 000 Daltons, even more preferably 1000-12 000 Daltons.

According to embodiment the invention is used in treatment of samples which contain scale inhibitor, and where the concentration of scale inhibitor is to be determined. The sample may thus be any industrial water system or industrial water system sample comprising at least one scale inhibitor. These industrial water systems where scale inhibitors may be employed include, but are not limited to, cooling tower water systems including open, recirculating, closed and once-through systems; petroleum wells, downhole formations, geothermal wells and other oil field applications; boilers and boiler water systems; mining process waters; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurisation water; water reclamation and purification systems; membrane filtration water systems; food processing streams, such as meat, vegetable, sugar beets, sugar cane, grain, poultry, fruit and soybean processing streams; and waste treatment systems as well as in clarifiers, liquid-solid applications, municipal sewage treatment and industrial or municipal water systems. Preferably the present method is used as a pre-treatment step for determining a concentration of at least one scale inhibitor in a sample originating from petroleum wells, downhole formations, geothermal wells and other oil field applications.

The method according to present invention is also suitable for use as a pre-treatment step for determining a concentration of residual polymer(s) from samples originating from enhanced oil recovery processes.

EXPERIMENTAL

Some embodiments of the invention are described in the following non-limiting examples.

Iron removal using hexacyanoferrate(II) was tested in synthetic brine having a composition given in Table 1.

TABLE 1

Brine composition

| Component | Concentration [g/l] |
|---|---|
| NaCl | 35.03 |
| MgCl2 × 6H2O | 1.46 |
| CaCl2 × 2H2O | 2.24 |
| KCl | 0.21 |
| BaCl2 × 2H2O | 0.13 |
| SrCl2 × 6H2O | 0.10 |

Chemicals used in Example 1 and their preparation were as follows

Deionized water (milliQ) which pH was adjusted to pH 2 by addition of 197 µl of 37% HCl to 200 ml of water Brine as defined in in Table 1. pH of the brine was adjusted to pH 2 by addition of 470 µl 37% HCl to 500 ml of brine Ascorbic Acid 0.5004 g of ascorbic acid was dissolved into 4.5 ml of deionized water $FeSO_4$ 1.2443 g of $FeSO_4 \times 7H_2O$ was dissolved into 25 ml of deionized water as defined above Hexacyanoferrate 1.8911 g of potassium hexacyanoferrate(II)$\times 3H_2O$ was dissolved into 25 ml of deionized water as defined above. The resulting pH of the solution was pH 5

Scale inhibitor

KemGuard 2253 (Kemira Oyj, Finland)

Example 1

Scale inhibitor was added in a dose of 102 ppm, which corresponds to a dose of 30 ppm, calculated as active component, to 50 ml of brine. Iron content of the brine samples was adjusted with $FeSO_4$. Hexacyanoferrate and ascorbic acid (reduction agent) were added to the samples according to the present invention. After that the amount of scale inhibitor was measured with a method employing time-resolved luminescence, as described in WO 2015/075308.

The results are given in Tables 2 and 3.

From the results shown in Tables 2 and 3 it can be seen that after the treatment with hexacyanoferrate and ascorbic acid the scale inhibitor could be determined from the liquid sample without interference of iron. The results were repeatable.

A constant hexacyanoferrate addition could be used for low iron content samples. However, a large excess of hexacyanoferrate might cause a slight interference. Addition of ascorbic acid does not interfere with the measurements.

TABLE 2

Results of Example 1.

| Test # | $FeSO_4$ [µl] | Ascorbic Acid [µl] | Hexacyano ferrate(II) [µl] | Filtered, 0.45 µm | Determined Scale Inhibitor, active [ppm] |
|---|---|---|---|---|---|
| 1 | — | 97 | 250 | yes | 28 |
| 2 | — | 97 | 625 | yes | 28 |
| 3 | — | 97 | 2500 | yes | 17 |
| 4 | 250 | — | 250 | yes | 26 |
| 5 | 250 | 97 | 250 | no | 17 |
| 6 | 250 | 97 | 250 | yes | 33 |
| 7 | 250 | 97 | 250 | yes | 31 |
| 8 | 250 | 97 | 2500 | yes | 12 |

TABLE 3

Results of Example 1.

| Test # | FeSO$_4$ [μl] | Ascorbic Acid [μl] | Hexacyano ferrate(II) [μl] | Filtered, 0.45 μm | Determined Scale Inhibitor, product [ppm] |
|---|---|---|---|---|---|
| 0 | — | 100 | — | yes | 97.8 |
| 1 | — | 100 | 250 | yes | 99.9 |
| 2 | — | 100 | 500 | yes | 90.0 |
| 3 | — | 100 | 750 | yes | 85.9 |
| 4 | — | 100 | 1000 | yes | 81.7 |
| 5 | — | 100 | 250 | yes | 102 |
| 6 | 250 | 100 | 300 | yes | 105 |
| 8 | 250 | 100 | 300 | yes | 102 |
| 9 | 250 | 1000 | 300 | yes | 101 |
| 10 | 250 | 5000 | 300 | yes | 98.4 |

Example 2

Chemicals used in Example 1 and their preparation were as follows
Deionized water (milliQ) which pH was adjusted to pH 2 by addition of 470 μl of 37% HCl to 425 ml of water
Brine as defined in in Table 1. pH of the brine was adjusted to pH 2 by addition of 37% HCl
Ascorbic Acid
0.2004 g of ascorbic acid was dissolved into 1.8 ml of deionized water
FeSO$_4$
0.6252 g of FeSO$_4$x7H$_2$O was dissolved into 12.5 ml of deionized water as defined above
Hexacyanoferrate
0.7502 g of potassium hexacyanoferrate(II)x3H$_2$O was dissolved into 10 ml of deionized water as defined above.
Scale inhibitor
KemGuard 2253 (Kemira Oyj, Finland)
Scale inhibitor was added to 25 ml of brine in variable amounts, the dose of active component varying from 1 ppm to 95 ppm. Iron content of the brine samples was adjusted with FeSO$_4$. Hexacyanoferrate and ascorbic acid (reduction agent) were added to the samples according to the present invention. After that the amount of scale inhibitor was measured with a method employing time-resolved luminescence, as described in WO 2015/075308.
The results are given in Table 4.

TABLE 4

Results of Example 2.

| Test # | Scale Inhibitor, active [ppm] | FeSO$_4$ [ul] | Fe [ppm] | Ascorbic acid [ul] | Hexacyano-ferrate(II) [ul] | Filtered 0.45 um | Determined Scale Inhibitor, active [ppm] |
|---|---|---|---|---|---|---|---|
| 1 | 1 | 250 | 50 | 100 | 300 | yes | 1 |
| 2 | 5 | 250 | 50 | 100 | 300 | yes | 4 |
| 3 | 15 | 250 | 50 | 100 | 300 | yes | 15 |
| 4 | 30 | 250 | 50 | 100 | 300 | yes | 28 |
| 5 | 95 | 250 | 50 | 100 | 300 | yes | 91 |
| 6 | 2 | 250 | 50 | 100 | 300 | yes | 2 |
| 7 | 3 | 250 | 50 | 100 | 300 | yes | 3 |
| 8 | 1 | 500 | 100 | 100 | 600 | yes | 1 |
| 9 | 1 | — | 0 | 100 | 300 | yes | 1 |

From the results shown in Table 4 it can be seen that after the treatment with hexacyanoferrate and ascorbic acid the scale inhibitor could be determined from the liquid sample without interference of iron even at low concentration. The results were repeatable.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for treating a liquid sample, the sample comprising iron in the form of iron (II) and/or iron (III) and at least one organic compound of interest, the method comprising
   (i) adding ascorbic acid to the sample in order to reduce any iron (III) in the sample to iron (II);
   (ii) after or simultaneous to the addition of ascorbic acid further adding a reagent comprising an ammonium salt, alkali metal salt or earth alkali metal salt of hexacyanoferrate to the sample;
   (iii) allowing the iron in the sample to interact with the reagent and to form an insoluble iron containing reaction product;
   (iv) separating the resultant insoluble reaction product comprising iron from the sample; and
   (v) determining the amount of the at least one organic compound of interest in the sample;
   wherein the method does not include the addition of any other reactants which promote the formation of another insoluble iron containing reaction product and/or the method does not include the removal of another insoluble iron containing reaction product from the sample.

2. The method according to claim 1, wherein the organic compound of interest is a synthetic organic compound, a natural polymer or a biopolymer.

3. The method according to claim 1, wherein the organic compound of interest is an organic compound selected from the group consisting of scale inhibitors, corrosion inhibitors, friction reducers, and polymers used in oil field applications or oil recovery processes.

4. The method according to claim 1, wherein the method comprises a step of adjusting pH of the sample to a pH value≤7, before addition of the reagent.

5. The method according to claim 1 wherein the reagent comprises hexacyanoferrate(II).

6. The method according to claim 1, wherein the reagent comprises ammonium or potassium hexacyanoferrate.

7. The method according to claim 5 wherein the molar ratio of hexacyanoferrate to iron in the sample ranges from 1:2 to 20:1.

8. The method according to claim 1, wherein the total concentration of iron is >0.5 ppm.

9. The method according to claim 1, wherein the method comprises separating the reaction product by filtering, centrifuging or sedimentation.

10. The method according to claim 1, wherein the method comprises adding a flocculation agent to the sample after addition of the reagent and separating the reaction product by flocculation.

11. The method according to claim 1, wherein the method comprises determining the amount of iron in the sample and adjusting the amount of reagent on basis of said determination.

12. The method according to claim 8, wherein the total concentration of iron is >75 ppm.

13. The method according to claim 12, wherein the total concentration of iron is >100 ppm.

14. The method according to claim 4, wherein the pH ranges from 3 to 5.

15. The method according to claim 4, wherein the pH ranges from 1 to 3.

16. The method according to claim 8, wherein the total concentration of iron ranges from 10 ppm to ≥50 ppm.

17. The method according to claim 5 wherein the molar ratio of hexacyanoferrate to iron in the sample ranges from 4:5 to 15:1.

18. The method according to claim 5 wherein the molar ratio of hexacyanoferrate to iron in the sample ranges from 1:1 to 10:1.

19. The method according to claim 1, wherein the insoluble reaction product is removed by filtration.

\* \* \* \* \*